United States Patent
Holmström

(10) Patent No.: US 6,236,873 B1
(45) Date of Patent: May 22, 2001

(54) ELECTROCHEMICAL SENSOR

(75) Inventor: Nils Holmström, Järfälla (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/147,901

(22) PCT Filed: Sep. 29, 1997

(86) PCT No.: PCT/SE97/01635

§ 371 Date: Aug. 9, 1999

§ 102(e) Date: Aug. 9, 1999

(87) PCT Pub. No.: WO98/14772

PCT Pub. Date: Apr. 9, 1998

(30) Foreign Application Priority Data

Sep. 30, 1996 (SE) .................................................. 9603569

(51) Int. Cl.$^7$ .................................................. G01N 27/00
(52) U.S. Cl. .................................................. 600/345
(58) Field of Search .................................. 600/345–350

(56) References Cited

U.S. PATENT DOCUMENTS 5,180,968  *  1/1993  Bruckenstein et al. ........... 204/153.1
5,562,815  *  10/1996  Priedel ................................. 204/415

* cited by examiner

Primary Examiner—Robert L. Nasser
(74) Attorney, Agent, or Firm—Schiff Hardin & Waite

(57) ABSTRACT

In a method and apparatus for eliminating the influence of double-layer capacitance in electrochemical measurements of the concentration of oxygen in blood using a working electrode, a reference electrode and a counter-electrode in contact with blood, a first potential is applied to the working electrode during a first measurement period and a second potential is applied to the working electrode during a second measurement period, the second potential being equal to a floating potential of the working electrode measured while the working electrode is in an electrically floating state. Charge generated by an output current from the working electrode respectively in the first and second measurement periods is accumulated, and the accumulated charge is used as a proportional representation of the amount of oxygen in the blood.

6 Claims, 4 Drawing Sheets

ELECTROCHEMICAL SENSOR

BACKGROUND OF THE INVENTION

1. The Field of the Invention

The invention relates to a method for eliminating the influence from the double layer capacitance charging on an electrical current measured using an electrochemical sensor or an electrode arrangement comprising one or more electrodes and a method for measurements of oxygen in blood in which method this elimination of the double layer is applied. The invention also relates to an apparatus for electrochemical measurements having means for eliminating the influence of the double-layer capacitance in measurements of concentrations and to the use of the apparatus according to the invention in conjunction with a pacemaker.

2. Description of the Prior Art

An electrochemical sensor normally comprises a working electrode (WE), a counter electrode (CE) and a reference electrode (RE)

In the description the following expressions are intended to have the following meaning:

Measuring potential: the applied potential, as related to a reference potential, during the measurement, in the description noted $\Phi$.

Floating potential: The potential, as related to a reference potential, an electrode will acquire when placed in an electrolyte and no current is allowed to pass through an outer circuit, i.e. not passing through the electrolyte, in the description denoted $E_0$.

It should be understood that these potentials actually refer to an arbitrarily chosen level, e.g. a common ground.

In the field of measuring electrical potentials in solutions one encounters the problem of assessing the influence of the double layer capacitance existing over the interface between the working electrode or sensor and the liquid phase.

There is, in general, a potential gradient across any interface separating two phases, e.g. a solid and a liquid phase, due to material constrants.

The potential difference across an interface may conveniently be pictured as an electrical double layer. One phase acquires a net negative charge (excess of electrons), and the other acquires a net positive charge (deficiency of electrons). Double layers exist not only at plane surfaces, but also surround solid particles suspended in a liquid medium. This double layer may be considered to be the equivalent of a simple parallel-plate capacitor. This phenomenon of course exists, e.g. at every electrode surface which is involved in any electro-chemical measurements.

Double layers of this kind are for instance discussed in Derek Pletcher, "A first course in Electrode Processes, pp 77–106, The Electrochemical Consultancy (Romsey) Ltd. (1991). The existence of the double layer and its influences on measurements made has two different aspects in Pacemaker Technology.

The first aspect is that a large influence from the double layer capacitance is sometimes a desired effect as is described in U.S. Pat. No. 4,602,637. A layer having a high double layer capacity, is provided at the phase boundary electrode/body fluids to minimize polarization rise during stimulation by roughening the surface of the passive electrode (counter electrode). This is also the object of the invention described in U.S. Pat. No. 4,611,604.

The second aspect is that in measurements in which more than one measurement electrical potential is used as related to a common value, e.g. a common ground it would be of interest to eliminate the influence of the double layer capacitance, since the influence of the double layer capacitance varies with the applied measurement potential and depends on concentration variations in the liquid of the entities, e.g. ions, dissolved gas etc. to be measured.

The method and the apparatus will be discussed and described with reference to measurements of oxygen dissolved in blood, but may be adapted to other measurements of the same type.

The measurements using electrochemical methods make use of the fact that the oxygen molecules dissolved in the blood are chemically reduced on the surface of the working electrode (WE) when the potential during a measurement pulse is forced to the negative potential (about 1 volt) relative to a reference electrode/potential. The counter electrode (CE) is herebelow assumed, at least partly, to have a surface made from carbon. In the reduction process, hydroxide ions are produced and the amount of these ions is dependent on the concentration of dissolved oxygen according to the reactions:

at the working electrode $2 H_2O+O_2+4 e^- \rightarrow 4 OH^-$ at the counter electrode $4 OH^- + C \rightarrow CO_2 + 2 H_2O + 4 e^-$ The above is simplified description of what is happening in the liquid. Other reactions may also take place.

The electrical current flowing to the working electrode WE during the measurement pulses is carried by the hydroxide ions. This current, called the oxygen current ($I_{pO2}$) is proportional to the amount of hydroxide ions formed on the surface of the working electrode (WE). During the measurement pulse the carbon coating of the counter British Specification 2 059 597 a method and an apparatus for determination of oxygen partial pressure measurements is described. The apparatus comprises an electrochemical cell having electrodes, in which successive electrical square wave polarizing voltage pulses are applied across the electrodes of the cell for measuring of the content of molecular oxygen diffusing through a membrane into the cell. The pulses results in currents through the cell having different waveforms during charging and discharging. It is recognized that there is an electrode drift with time. Thus a correction factor to be applied in the measurements has to be used. The correction factor is calculated using the integrated value of one charge waveform and a succeeding discharge waveform.

PCT Application WO 83/01687 concerns a method and apparatus for pulsed electroanalyses of an electroactive material in an electrolyte by using a cell and applying pulses of an On-potential and an Off-potential. The On- potential is chosen to give a Faradaic current and the Off-potentials is chosen such that no Faradaic current is present. The current is integrated for the time the On-potential is applied and at least part of the time when the Off-potential is applied and the integral is used for concentration measurements. An object of the invention is to eliminate the effect of the double layer formed.

Electrochemical determination of the oxygen concentration, particularly in biological matter, is also the subject of U.S. Pat. No. 4,853,091. A method and an apparatus for measurements over long periods of time is described in which use is made of three electrodes, a working electrode (WE), a reference electrode and a counter electrode (CE). Two potentials are cyclically applied to the working electrode with one potential (measuring potential) in the range $-1,4 \ V \leq \rho Ag/AgCl \leq -0,4 \ V$ and the other potential, the recovery potential in the range 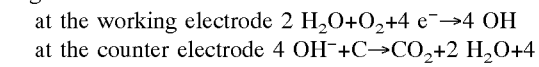 $-0,2 \ V \leq \rho Ag/AgCl \leq +0,2 \ V$. At the recovery potential, there will be no oxygen current depending on the fact that the chosen potential will not be of a magnitude as to allow a reduction of oxygen at the working electrode.

However, there will still be a double layer forming on the electrode/s, which is dependent on the applied potential (conf. above), but this double layer will not exhibit the same capacitance as the double layer present when the measuring potential is applied. This problem is according to the cited patent solved by starting the measurement period some time after the measurement potential is applied in order to avoid the current induced by the changes in the double layer resulting from the application of the measurement potential. The problem is that it is not possible to decide when the influence from the double layer ceases to exist.

SUMMARY OF THE INVENTION

An object of the invention is thus to minimize the influence of the charging of a double layer capacitance when measurement are performed in a fluid, e.g. measurements of the oxygen content in blood or body liquids.

Another object of the invention is to increase the sensitivity of the measurements.

Yet another object is to reduce as much as possible of the amount of energy used for the measurements and to attain a more relevant value than has been possible up to now.

The above objects are achieved in a method and apparatus in accordance with the invention wherein the working electrode is initially placed in an electrically floating state and the floating potential of the working electrode, relative to the reference electrode, is sampled and held, the working electrode is subsequently placed at a first potential relative to the reference electrode during a first predetermined measuring period $t_1$ to $t_2$, during which the first potential is sufficient to cause an electrochemical reaction at the working electrode, the working electrode is subsequently placed at a second potential relative to the reference electrode which is equal to the sampled and held floating potential during a second measurement period $t_2$ to $t_3$ immediately following and equal to the first measuring period, a first charge $Q_1$ is calculated which is produced during the first measurement period starting at a time $t_i$ after $t_1$, with $t_1 < t_i < t_2$ and a second charge $Q_2$, of opposite polarity to $Q_1$, is calculated during the second measurement period at the time $t_i$ after $t_2$, with $t_2 < t_i < t_3$, and wherein a difference $\Delta Q$ is formed by adding $Q_1$ and $Q_2$, this difference $\Delta Q$ being proportional to an amount of oxygen in the blood.

A method and an apparatus for measuring a concentration of a substance, i.e. oxygen in blood according to the invention thus has a number of advantages. The sensing will be accurate, since the influence of the double layer capacitance virtually will be eliminated by mathematically adding one measurement value to another, each of which contains a part which is dependent on the double-layer capacitance, but these values measured in such a way that these parts have different signs and thus these parts will cancel each other out.

The invention also ensures that immediately before each measurement the apparatus will be at a given potential (below floating potential), which depends on the material in the working electrode, and the liquid medium iin which it is placed. This will make the measurements and the calculations/evaluations of the measurements very easy and give a high accuracy in the time perspective.

The method and apparatus will thus prove to be beneficial in several other ways. Between the measurements, the working electrode will be at a floating potential relative to the reference electrode. The floating potential is the potential at which there is no electrical connection between the working electrode and the reference and counter electrodes in the apparatus, i.e. no emf is applied to the electrodes forcing a current through the measurement cell, and thus there will be no electrical current flowing through the working electrode. This in turn saves energy and as well as in the case of measurements made in the blood stream or in the body fluids, preventing unnecessary depletion of oxygen in the close proximity of the working electrode.

The method and the apparatus also allow an implanted oxygen sensor according to the invention to be used in connection with implanted pacemakers by reducing the energy demand for this type of measurements. The method and the apparatus also provide another advantage in that the measuring pulses through the method according to the invention can be made so short such as to give a possibility of synchronizing the measurements with the heart cycle, i.e. an ability to measure within one cycle.

The method and device thus will improve the measurements by minimizing the variations in the measured values caused by the long and short time variations in the floating potential of the working electrode, e.g. the temperature, the pressure of the gases present, the adsorption of the electrode surface, etc.

It is a known fact within the art that the surfaces of sensors and electrodes which are implanted and electrically active invariable will become at least partly covered with protein particles etc. This effect will be minimized by minimizing the measurement period and by the manner in which the working electrode will be left "floating". This will in turn result in a longer life for the electrode itself and will secure a longer period of more precise and accurate measurements.

The simplicity of the apparatus according to the invention and the simplicity of the measurements and the evaluation of the same will prove the invention to be useful for measurements in which high reliability is necessary and during time periods of maybe several years in which the measurements are activated by indications chosen for the specific application.

DESCRIPTION OF THE PREFERRED EMBODIMENTS

In all of the figures, all potentials are measured relative to 0 V, i.e. a common ground. The working electrode WE is held at 0 V by an operational amplifier E3.

Figure 1A:
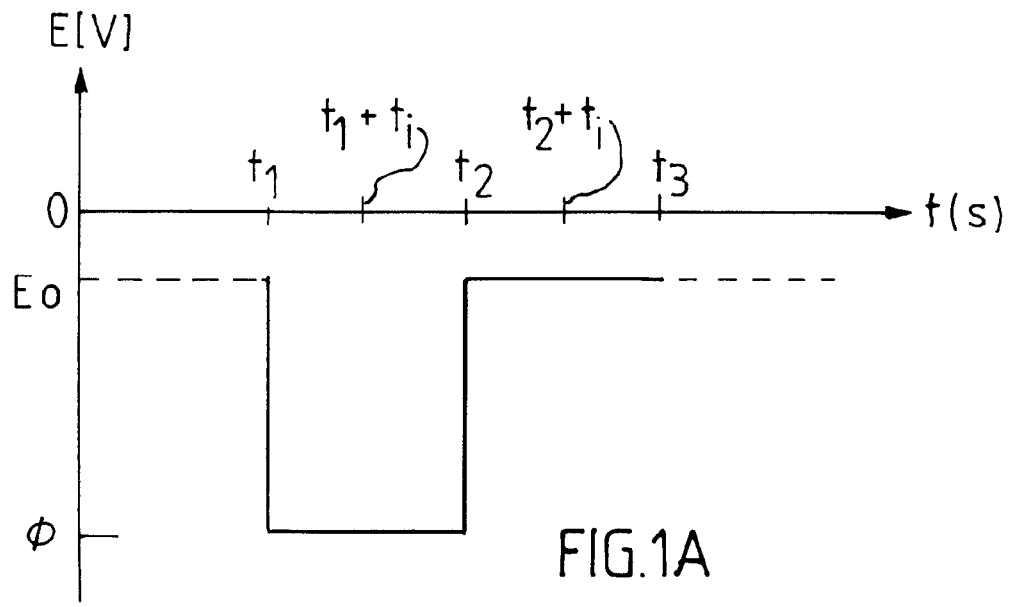
FIG. 1A is a voltage/time diagram.

FIG. 1A shows the potential on the working electrode WE related to the reference electrode RE, when the working electrode WE is free-floating, denoted $E_0$ and when the measurement potential Φ is applied to the same. Φ is chosen as to be equal or to exceed the reduction potential of oxygen. In the diagram the potential on the electrode WE, when free-floating, is shown as a dashed line up to the time $t_1$ and after $t_3$. This potential $E_0$ is memorized just before $t=t_1$. Between $t_1$ and $t_2$ a measuring potential (e.g. the reduction potential of oxygen) is applied to the WE and at $t_2$ the potential on the WE is forced back to said memorized potential $E_0$ and kept there until $t=t_3$. After $t=t_3$ the WE is returned to the free-floating state. This is one measurement cycle.

It should of course be realized that there must be different potential, also related to the RE, present on the counter electrode CE, which will enable a corresponding reaction to occur at the CE in accordance with the above description as to the reactions taking place at the WE and CE. However, the absolute value of this potential is not of interest in the actual measurements, as they are related only to the reaction at the WE.

Figure 1B:
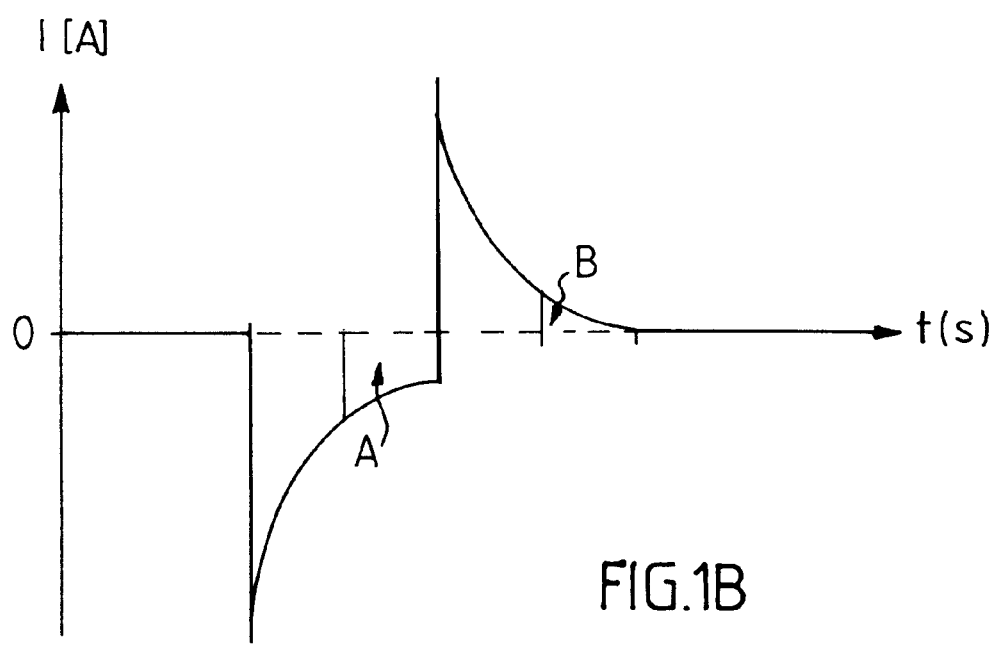
FIG. 1B is a current/time diagram, for explaining the basic inventive concept.

FIG. 1B shows the time/current relationship corresponding to the potential changes on the working electrode WE. The areas denoted A and B are used in the calculations.

The measurements are performed during a short period, e.g. 1–30 ms. In relation to this the time that the working electrode WE is free-floating is e.g. 0.5–10 s. The potential of the WE is forced to the reduction potential Φ, vs. the reference electrode, from $t=t_1$ to $t=t_2$ and the electrical current produced is integrated from $t=t_1+t_i$ to $t=t_2$. This integration corresponds to a charge Q1 corresponding to the area A in FIG. 1,b. Then the current incurred by the potential which is being forced back to $E_0$ from $t=t_2$ to $t=t_3$ is integrated from $t=t_2+t_i$ to $t=t_3$ and the corresponding charge $Q_2$ is shown as the area B in FIG. 1b.

On account of the potential of the WE being forced back to its memorized floating potential after the pulse, the magnitude of the two potential steps will be the same, and hence the cathodic and the anodic part of the current related to changing of the double layer capacitance will be the equal. That means that if we substract B from A, i.e. $Q_2$ from $Q_1$, the remaining charge only relates to mass transport in the liquid (electrolyte).

Figure 2:
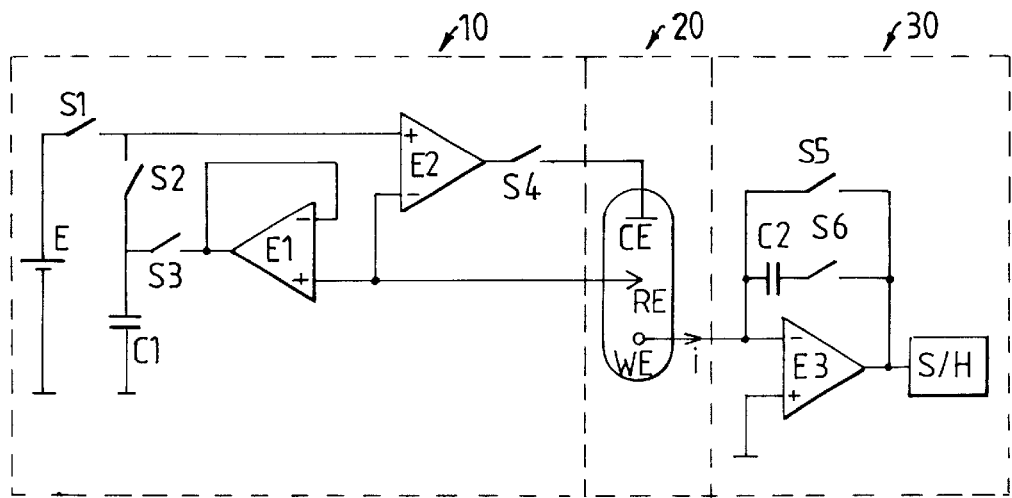
FIG. 2 is a circuit diagram of a first embodiment according to the present invention.

A preferred apparatus for accomplishing these measurements is shown in FIG. 2. The circuit diagram in FIG. 2 comprises three main parts. Part 10 comprises the circuitry connected with the counter electrode CE and the reference electrode RE. Part 20 comprises the liquid medium (the electrolyte) in which the two named electrodes are immersed together with the working electrode WE. Part 30 comprises the circuitry connected to the working electrode WE. This part also comprises a sample and hold circuit S/H. Such sample and hold circuits are well known within the art and are thus not described in more detail.

Part 10 has a voltage source E, the positive terminal of which is connected to a switch S1. The negative terminal of the voltage source E is connected to a common ground. A capacitor C1 and a switch S2 are coupled together in series and are in parallel with the voltage source E and the switch S1. The capacitor C1 is connected on one side to the common ground.

The non-inverting input of an operational amplifier E2 is connected to a point between the switches S1 and S2. The inverting input of the same amplifier E2 is coupled to the reference electrode RE and to the non-inverting input of a voltage follower E1. The output of the operational amplifier E2 is coupled via a switch S4 to the counter electrode CE.

The output of the voltage follower E1 is coupled via switch S3 to a point between switch S2 and capacitor C1.

Part 20 comprises the electrodes and the medium in which the measurements are to take place.

The working electrode WE is connected to the inverting input of an operational amplifier E3 in circuit part 30. The non-inverting input of the same is connected to the common ground. Parallel to the output of E3 and the inverting input of the same a capacitor C2 and a switch S6 are arranged in series. A switch S5 is connected in parallel over the capacitor C2 and the switch S6. A sample and hold circuit is connected to the output of the operational amplifier E3.

The device in FIG. 2 may be viewed as having five different modes depending on the settings of the switches S1 to S6. The potential of the working electrode WE is always held at 0 V (common ground) using the operational amplifier E3. The five modes are described in relation to FIGS. 3A through 3E, 4 and 5.

Figure 3A:
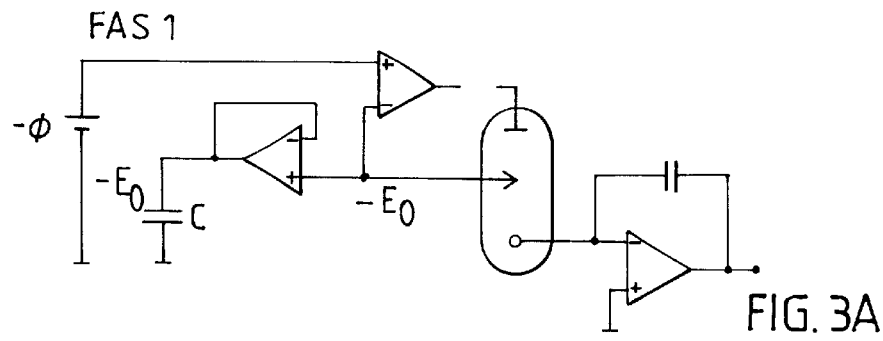
FIGS. 3A through 3E respectively show equivalent circuit diagrams for the five modes of a measurement cycle in accordance with the invention.

In mode 1, shown in FIG. 3A in which the working electrode is in the floating state between the measuring pulses the setting of the switches is as follows (where 0 signifies open switch and 1 signifies closed switch):

S1=1, S2=0, S3=1, S4=0, S5=0, S6=1.

The potential on the reference electrode (RE) is applied to the input terminal of the voltage follower E1, the output of which is connected to the capacitor C1, which accordingly is charged to the floating potential of the reference electrode (RE) with reference to the working electrode (WE). The value of this floating potential is memorized in C1 at the time when S3 is opened, i.e. when time t is reset to $t_1$.

The counter electrode (CE) is floating, i.e. no current passes through the counter electrode (CE) since the circuit is open.

In mode 1 there is a constant voltage over the capacitor C2, which is also present on the output terminal of E3 This voltage corresponds to the previous measurement made.

Figure 3B:
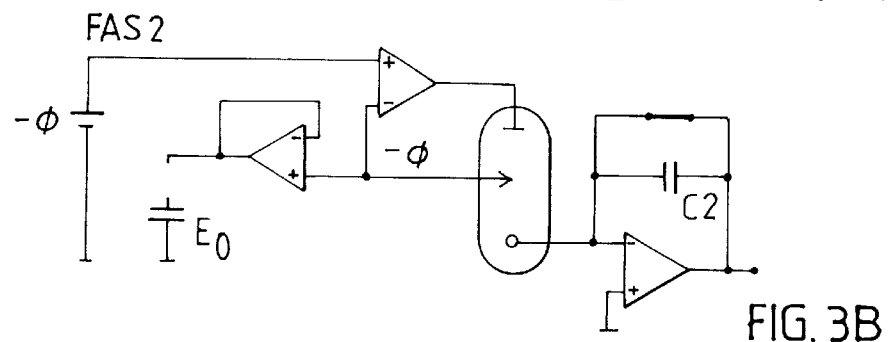

In mode 2, shown in FIG. 3B, the switches are set as follows:

S1=1, S2=0, S3=0, S4=1, S5=1, S6=1

Capacitor C1 holds the floating potential of the reference electrode.

Operational amplifier E2 is now connected to the counter electrode (CE). On the non-inverting input the measuring potential $-\phi$ is present and on the inverting input terminal the potential of the reference electrode (RE) is present. The current through CE is controlled by the operational amplifier E2 being arranged such that the potential on the non-inverting and inverting inputs will be the same through negative feedback. Thus the working electrode WE exhibits the potential $\phi$ related to the reference electrode (RE) e.g. if $\phi=0,8$ V, which is a normal reduction potential for $O_2$, then the potential step which is established has the amplitude $-(E_0-\phi)$.

The capacitor C2 is discharged via the switches S5 and S6 (reset of C2).

Figure 3C:
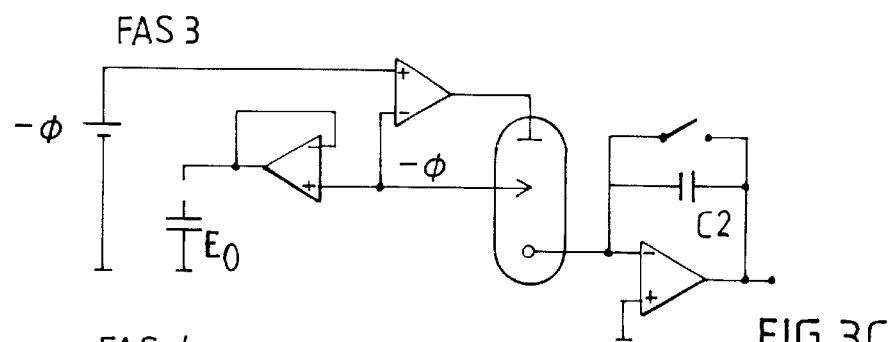

In mode 3, shown in FIG. 3C the setting is as follows:

S1=1, S2=0, S3=0, S4=1, S5=0, S6=1

This mode resembles mode 2 except in this mode the switch S5 is open, so that the measuring current by charging C2 is integrated from the time $t=t_1+t_i$ to the time $t=t_2$ according to formula (1):

$$Q_1 = \int_{tI-n}^{t2} i(t)dt \quad (1)$$

thus giving the charge $Q_1$ on C2

If e.g. reduction of oxygen is occurring, then the current i may be written as the sum of two currents $i(t)=i_p(t)+i_d(t)$, where $i_p(t)$ is the current arising from the reduction of oxygen gas while $i_d(t)$ is the current arising from the "forming of the double layer or charging" of the double layer capacitance at the potential $-(E_0-\phi)$ as above.

Figure 3D:
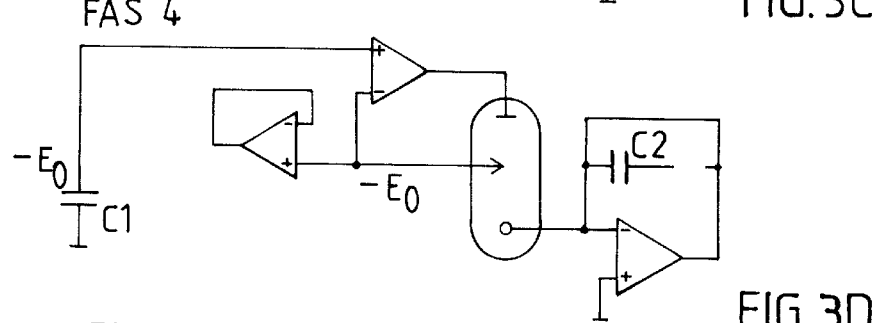

In mode 4, shown in FIG. 3D, the switches are set as follows:

S1=0, S2=1, S3=0, S4=1, S5=1, S6=0

In this mode the positive terminal of E2 is connected to capacitor C1, which is charged to the memorized floating potential $E_0$. The counter electrode CE is controlled by the operational amplifier E2 such that the reference potential equals $E_0$. The potential step thus will equal $+(E_0-\phi)$, i.e. the same amplitude but the opposite polarity to that at the beginning of mode 2.

The current is shunted in parallel over the capacitor C2 via the switch S5, such that the voltage applied over C2 remains unchanged.

Figure 3E:
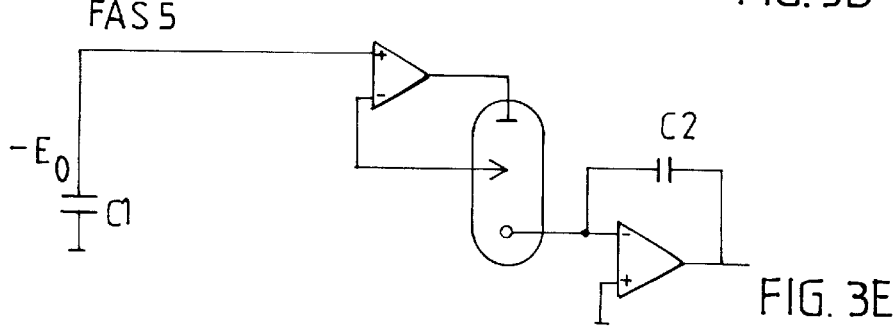

In mode 5, shown in FIG. 3e, the setting is as follows:

S1=0, S2=1, S3=0, S4=1, S5=0, S6=1

In this mode the only change in the setting of the switches is that S5 is open and S6 is closed. The current which is discharging the electrochemical double layer (the double layer may be thought of as a virtual capacitance) charges C2 and a charge $Q_2$ is added to the charge $Q_1$ already established in the capacitor C2 during mode 3.

$$Q_1 = \int_{t1-n}^{t2} i(t)dt \quad (1)$$

$$Q_2 = \int_{t2-n}^{t3} i_d(t)dt \quad (2)$$

Taken that $t_2-t_1=t_3-t_2$ and $t_i$ being a chosen predetermined time constant (3)
i.e. integration is performed for equal lengths of time after each change in potential $$Q = Q_1 + Q_2 = \int_{t_1-n}^{t2}(i_p(t)+i_d(t))dt + \int_{t_2+n}^{t_1} -i_d(t)dt = \int_{t_1-t_i}^{t2} i_p(t)dt \quad (4)$$

At the floating potential $E_0$ there exists no oxidation or reduction reaction at the electrode interface, which means that the current there depends only on the charging/discharging of the double layer capacitance.

This adding of charges, as the potential changes from $E_0$ to $\phi$ and back to $E_0$ related to the reference electrode and the integrating of the current through C2 is started at a time $t=t_1+t_i$ at a predetermined time after the potential step to $t=t_2$, respectively at a time $t=t_2+t_i$ to $t=t_3$ during the next potential step will thus in reality result in that the charge present on C2 will effectively diminish since the potential differences inducing the charges $Q_1$ and $Q_2$. respectively, are reversed with respect to each other, thus, the parts of the charges stemming from the double layer will cancel out.

Thus the end voltage over C2 will according to the following formula (3) be proportional to:

$$U \equiv \frac{Q}{C_2} \quad (5)$$

This value can thus be the value taken as a measure of the amount of e.g. oxygen in blood.

Figure 4:
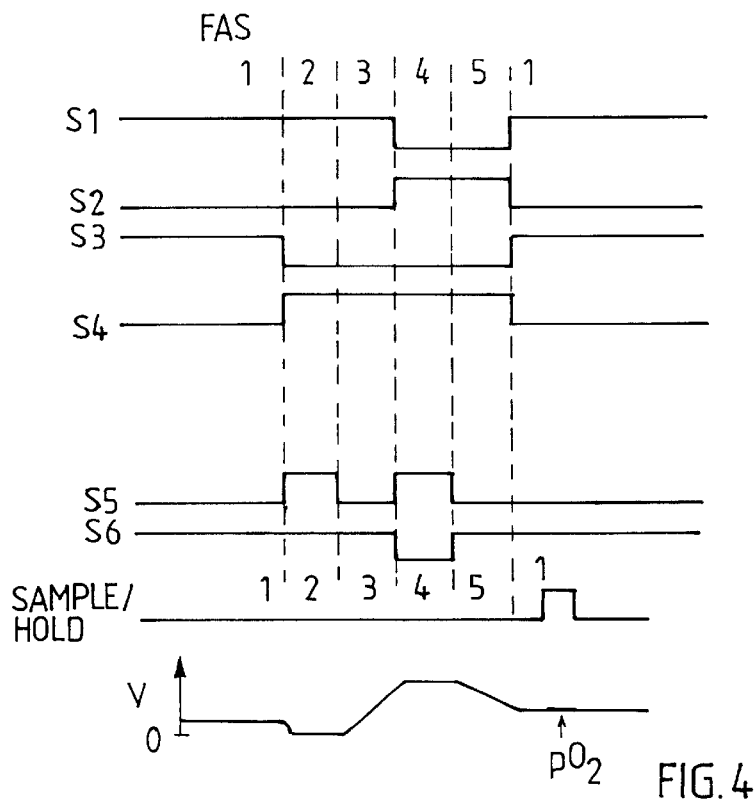
FIG. 4 is a diagram showing the five modes of the first embodiment illustrating the open/closed states of the switches S1–S6 related to a time scale.

The setting of the switches and the function of the sample and hold circuit are also illustrated in FIG. 4 as related to the five different modes and at the bottom of the figure the potential over C2 is shown as i varies over time. In mode 1 the voltage over C2 corresponds to the potential resulting from the previous measurement, in mode 2 the voltage over C2 will be 0, in mode 3 the potential corresponds to the voltage over C2 during the first measurement period, in mode 4 the current passes in parallel to the C2 and the voltage remains the same and in mode 5 the potential on the measuring electrode is forced back to the freefloating state, which leaves a voltage over C2 corresponding to the oxygen-dependent current.

Figure 5:
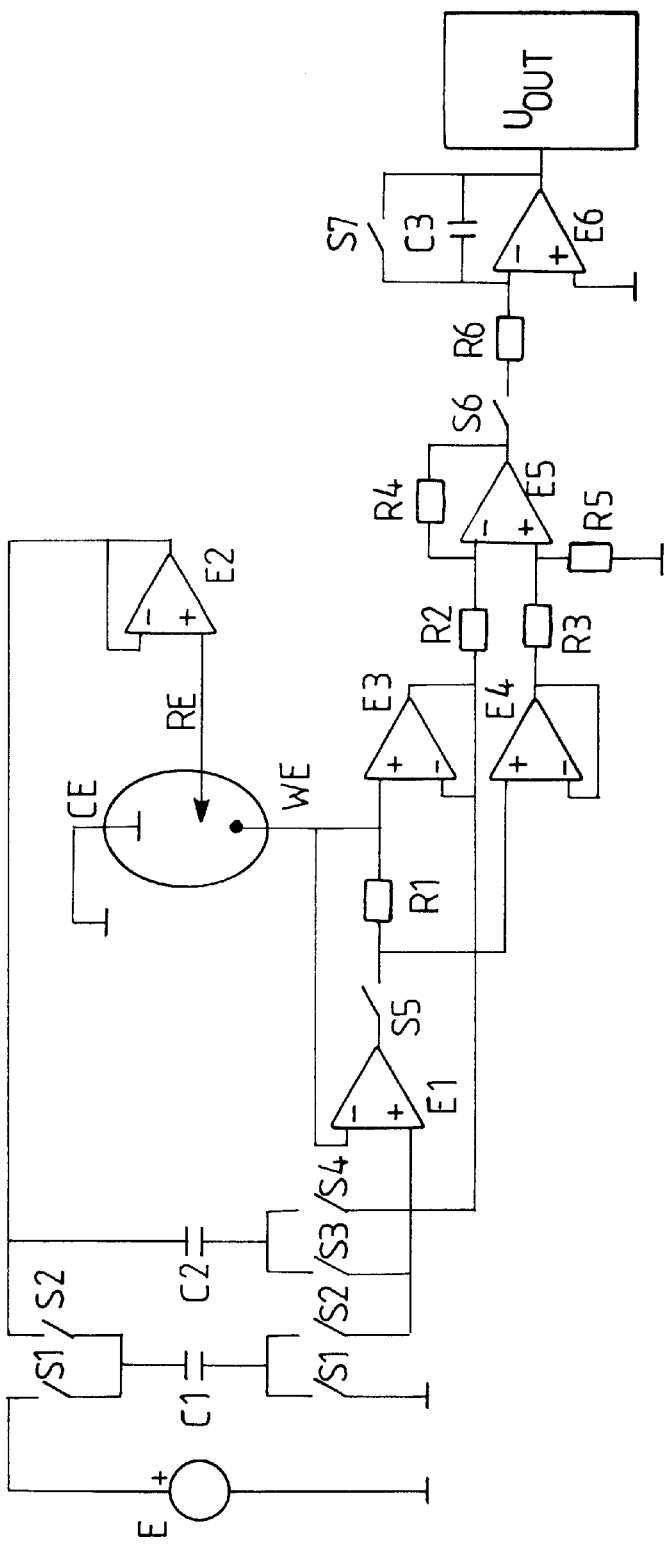
FIG. 5 is a circuit diagram of a second embodiment according to the present invention.
Figure 6:
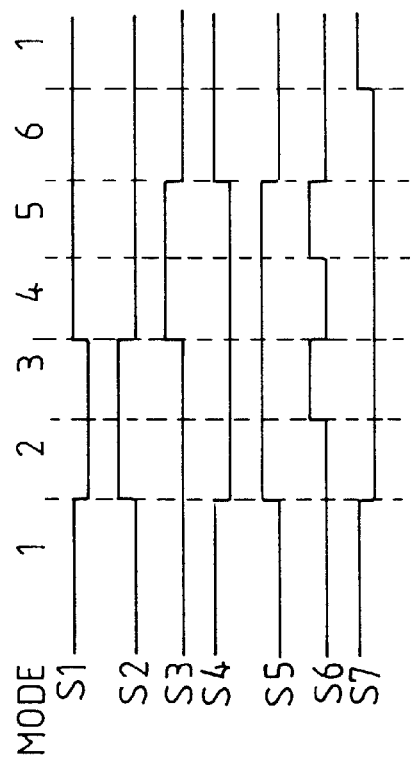
FIG. 6 is a diagram showing the six modes of the second embodiment illustrating the open/closed states of the switches S1–S7 related to a time scale.

A second embodiment of the invention is shown in FIGS. 5 and 6, where in FIG. 5 the second embodiment is show in which the counter electrode is connected to common ground (0V). The circuitry comprises power source E, on the negative side connected to common ground and on the other side to a switch S1. Over the power source E two capacitors C1 and C2 are connected in parallel. Two switches S1 and S1' connect C1 with the power source E and to ground, resp., moreover two switches 2 and 2' connect C1 to the rest of the device. Capacitor C2 connected in parallel to C1 can be connected/disconnected via switch S2 to C1 and via S3 to the circuitry connected to the working electrode WE. S2' and S3 are connected to the non-inverting input of an operational amplifier E1, the inverting input of the same connected to the working electrode WE. A switch S4 connects/disconnects C2 from a differential amplifier, which consist of two voltage followers E3 and E4, one operational amplifier E5, five resistors R2, R3, R4 and R5. Switch S4 is connected to the inverting input of E3, the output of E3 and to R2, S2', S3' are connected to the non-inverting input of E1, the inverting input of which is connected to WE. The output of E1 is via S5 connected to one side of a resistor R1, the other side of which is connected to the non-inverting input of E3. The working electrode is also connected to a point between the resistor R1 and the non-inverting input of E3

The output of E3 is connected to the inverting input of the same and to one side of R2, the other side of which is connected to the inverting input of E5 and to resistor R4, the other side of which is connected to the output of E5 and to a switch S6, which in turn connects to one side of a resistor R6. The non-inverting input of E4 is connected to a point between S5 and R1. The inverting input of E4 is connected to the output of the same. The output of E4 is also connected to the non-inverting input of E5 via a resistor R3. The non-inverting input of E5 is connected to ground via a resistor R5.

The resistor R6, connected to switch S6 after the signal amplifier, is on the other side connected to the inverting input of an operational amplifier E6. A switch S7 and a capacitor C3 are connected in parallel over the non-inverting input of E6 and the output of the same. The non-inverting input of E6 is connected to ground.

In FIG. 6 the setting of the switches during the 6 modes are shown.

In mode 1 there will be no current floating to or from the working electrode (WE), and thus no voltage over the resistor R1. C2 is charged to the desired next measurement potential and C2 is charged to floating potential of the working electrode. (The voltage present between the outputs of E2 and E3.) C3 is shortened by S7 and the outvoltage will be 0V.

In mode 2 S5 is closed. The operational amplifier E3 adjusts the potential of the WE to the measurement potential (compared to the RE), the voltage drop over R1 is measured by the differential amplifier (E3, E4,E5,R2,R3,R4 and R5).

In mode 3 S6 is closed and the current is integrated on 3.

In mode 4 the memorized potential on C2 is now used to control the working electrode potential.

In mode 5 S6 is closed and the current is again integrated on C3. The sign is however normally opposite which reduces the voltage over C3.

In mode 6 the measured value is held on the output of E6 and may be sampled and held and used for intended purposes. The output voltage Uout can be expressed as $$Uout = \frac{R1}{C3*R6}\left(\int_{t_1+t_i}^{t_2} i_1(t)dt + \int_{t_2+t_i}^{t_1} i_2(t)dt\right) \quad (6)$$

The method and apparatus according to the invention is thus very well suited to be used with e.g. pacemakers in order to sense the oxygen level in the blood and using the sensed value in order to control the pacing. As the measurement will be comparable over time and also as there also is a possibility to by programming or in other ways to decide on when and how often measurements are to be made the device will be satisfying from the standpoint of energy consumption and reliability.

Although modifications and changes may be suggested by those skilled in the art, it is the intention of the inventor to embody within the patent warranted hereon all changes and modifications as reasonably and properly come within the scope of his contribution to the art.

What is claimed is:

1. A method for eliminating an influence of double-layer capacitance in an electrochemical measurement of a concentration of oxygen in blood, comprising the steps of:

providing a working electrode, a reference electrode and a counter-electrode in contact with blood;

placing said working electrode in an electrically floating state so that said working electrode is at a floating potential relative to said reference electrode;

sampling and holding said floating potential of said working electrode;

subsequently placing said working electrode at a first potential relative to said reference electrode during a first predetermined measurement period $t_1$ to $t_2$, said first potential being sufficiently high to cause an electrochemical reaction at said working electrode;

subsequently placing said working electrode at a second potential relative to said reference electrode equal to the sampled and held floating potential during a second measurement period $t_2$ to $t_3$ immediately following and equal in length to said first measurement period;

identifying a first electrical charge $Q_1$ produced during said first measurement period starting at a time $t_i$ after $t_1$, with $t_1 < t_i < t_2$ and identifying a second electrical charge $Q_2$ of opposite polarity to $Q_1$ during said second measurement period at said time $t_i$ after $t_2$, with $t_2 < t_i < t_3$;

forming a difference $\Delta Q$ by adding $Q_1$ and $Q_2$, and using $\Delta Q$ as a proportional indicator of an amount of oxygen in said blood.

2. A method as claimed in claim 1 wherein the step of sampling and holding said floating potential comprises sampling and holding said floating potential of said working electrode in a capacitor.

3. A method as claimed in claim 1 wherein the step of identifying said first electrical charge $Q_1$ and said second electrical charge $Q_2$ and forming said difference $\Delta Q$ comprise charging a capacitor starting at time $t_i$ during said first measurement period, with a charge on said capacitor at an end of said first measurement period being $Q_1$, and maintaining said charge $Q_1$ on said capacitor and charging said capacitor starting at said time $t_i$ in said second measurement period, with a charge on said capacitor at an end of said second measurement period being $Q_1+Q_2$.

4. An apparatus for eliminating an influence of double-layer capacitance in an electrochemical measurement of a concentration of oxygen and blood, comprising:

a working electrode;

a reference electrode;

a counter-electrode, each of said working electrode, said reference electrode and said counter-electrode being in contact with blood;

means for measuring a floating potential at said working electrode, relative to said reference electrode, when said working electrode is in an electrically floating state, and for temporarily retaining said floating potential;

means for placing said working electrode at a first potential relative to said reference electrode during a first predetermined measurement period $t_1$ to $t_2$ and thereby causing an electrochemical reaction at said working electrode;

means for placing said working electrode at a second potential relative to said reference electrode, equal to said retained floating potential, during a second measurement period $t_2$ to $t_3$ immediately following and equal to said first measurement period;

means for identifying a first electrical charge $Q_1$ producing during said first measurement period starting at a time $t_i$ after $t_1$, with $t_1 < t_i < t_2$ and for identifying a second electrical charge $Q_2$ of opposite polarity to $Q_1$ during said second measurement period at said time $t_i$ after $t_2$, with $t_2 < t_i < t_3$; and means for forming a difference $\Delta Q$ by adding $Q_1+Q_2$, with $\Delta Q$ being proportional to an amount of oxygen in said blood.

5. An apparatus as claimed in claim 4 wherein said means for measuring and retaining said floating potential comprises a capacitor connected across said working electrode while said working electrode is in said electrically floating state.

6. An apparatus as claimed in claim 4 wherein said working electrode produces an output current during each of said first measurement period and said second measurement period, and wherein said means for identifying said first electrical charge $Q_1$ and said second electrical charge $Q_2$ and said means for forming said difference $\Delta Q$ comprise a capacitor supplied with said output current from said working electrode during each of said first measurement period and said second measurement period, with no intervening discharge of said capacitor.

* * * * *